United States Patent [19]
Behney

[11] 4,332,250
[45] Jun. 1, 1982

[54] EQUINE SANITATION APPARATUS AND METHOD

[76] Inventor: Charles A. Behney, P. O. Box 4337, Bisbee, Ariz. 85603

[21] Appl. No.: 164,785

[22] Filed: Jul. 7, 1980

[51] Int. Cl.[3] A61M 3/00

[52] U.S. Cl. 128/239; 128/248; 401/282

[58] Field of Search 128/239, 227, 224, 251, 128/248; 401/203, 282, 206, 207

[56] References Cited

U.S. PATENT DOCUMENTS

| | | | |
|---|---|---|---|
| 895,472 | 8/1908 | Knickerbocker et al. | 401/203 |
| 2,225,101 | 12/1940 | Conk et al. | 401/203 |
| 2,559,757 | 7/1951 | Chandler | 401/285 X |
| 2,576,766 | 11/1951 | Sokolik | 128/251 X |
| 3,009,190 | 11/1961 | Awot | 401/282 X |
| 3,459,175 | 8/1969 | Miller | 128/239 X |
| 3,709,224 | 1/1973 | Fielding | 128/239 |

*Primary Examiner*—John D. Yasko
*Attorney, Agent, or Firm*—Gerlach, O'Brien & Kleinke

[57] ABSTRACT

Equine sanitation apparatus includes a supply tube, and in succession on the tube, a nozzle at its distal end, a sponge, and structure for manipulating the apparatus, whereby the nozzle and the sponge may be inserted into a body cavity and the sponge manipulated therein, and liquid may be supplied to and exhausted from the body cavity via the tube and the nozzle. The preferred apparatus includes a syringe-type instrument for supplying liquid to the tube and exhausting the liquid therefrom. The apparatus advantageously is employed in a method for cleaning an equine sheath, wherein the nozzle and the sponge are inserted in the sheath, the sheath cavity is flushed through the tube and the nozzle to loosen and remove smegma therein, and the interior surface of the sheath is scrubbed with the sponge to break up crustaceous smegma for removal thereof.

19 Claims, 12 Drawing Figures

EQUINE SANITATION APPARATUS AND METHOD

BACKGROUND OF THE INVENTION

This invention relates to equine sanitation apparatus and a sanitation method. More particularly, the invention relates to apparatus for insertion into a body cavity and then cleaning the cavity therewith, and to a sheath-cleaning method which may be performed therewith.

The sheath of the male horse is prone to accumulate in the cavity thereof a mixture of body oil, dirt, salt and water, referred to collectively as "smegma," which renders the area unsanitary and increases the susceptibility to infection and to the transmittal of infectious organisms. The accumulation occurs especially if the penis is not dropped or is dropped incompletely for urination, and it occurs in animals of all ages, from colts to mature horses, especially geldings. It may occur in stallions, although the occurrence is less likely with increasing breeding activity. It is advisable to clean colts and geldings periodically, and stallions are cleaned between breedings.

A common method of cleaning a sheath is to soak a sponge with an aqueous emulsion or solution of a soap or shampoo that cuts or emulsifies the body oil while also removing dirt, salt, and any other debris, and washing the internal surfaces of the sheath with the sponge. The sponge is held in one hand, and both the sponge and the hand are inserted in the sheath cavity. One disadvantage of this method is that by the time the sponge is inside the sheath, most of the soapy water has been squeezed out. The hand must be inserted with the sponge for on the order of 10 to 20 times, in order to adequately clean the sheath, especially when relatively hard, crustaceous smegma is present, as occurs commonly adjacent to the mouth of the sheath.

A serious disadvantage of the foregoing method is that the individual doing the cleaning is in great danger of being kicked, especially when a stallion is being cleaned. In order to avoid the problem of kicking, a tranquilizer may be given to the animal, and it drops the penis for relatively easy cleaning. However, some horses react to tranquilizers, suffering an allergic reaction and/or becoming permanently disabled in that they are never again able to retract the penis. Lesser disadvantages are that it is necessary to bring the animal to a veterinarian for the administration of a transquilizer, and after performing the cleaning operation, there may be a delay before the animal can be moved.

SUMMARY OF THE INVENTION

The present invention provides a sanitation apparatus and method which overcome the disadvantages of the foregoing prior method and provide marked improvements thereover. Employing the new apparatus to perform the new method, the sheath is thoroughly and efficiently cleansed, while the operation is such that the animal is not bothered and the danger of being kicked is substantially obviated.

Moreover, the apparatus can be handled and the method performed by the owner of the animal as well as by a veterinarian. Inasmuch as the danger of kicking is obviated, it is not necessary to use tranquilizers and expose the animal to the risks thereof, and the animal may be cleansed regularly in its stables.

The apparatus may be made economically and, consequently, may be disposable. Alternatively, the apparatus may be constructed for repeated use, especially for use by veterinarians.

The sanitation apparatus of the invention includes a supply tube having distal and proximal ends, nozzle means on the distal end of the tube, manipulating or handle means on the tube and spaced apart longitudinally from the nozzle means in the direction of the proximal end of the tube, and a sponge on the tube between the nozzle means and the manipulating means, whereby the manipulating means may be manually operated to insert the nozzle means and the sponge into a body cavity and manipulate the sponge therein, and a liquid may be supplied to and exhausted from the body cavity via the tube and the nozzle means. The preferred apparatus also includes in the combination, a liquid supply instrument for supplying a liquid to the tube and exhausting the liquid therefrom.

The new method of the invention for cleaning internally an equine sheath includes the steps of inserting in the sheath a sponge having a liquid supply tube extending therethrough for discharge into the sheath from a distal end of the tube, flushing the interior of the sheath with liquid delivered through the tube to loosen and remove smegma in the sheath, and scrubbing the interior surface of the sheath with the sponge to break up crustaceous smegma for removal thereof. In the preferred method, the sheath flushing is effected by delivering liquid into the sheath from nozzle means on the distal end of the tube, which nozzle means directs the flow of liquid from the tube so as to avoid impingement of a liquid stream therefrom directly upon the organ in the sheath.

BRIEF DESCRIPTION OF THE DRAWINGS

The drawings illustrate preferred embodiments of the apparatus and the method of the invention, without limitation thereto. In the drawings, like elements are identified by like reference symbols in each of the views, and.

DESCRIPTION OF THE PREFERRED EMBODIMENTS

Figures 1, 2, 3:
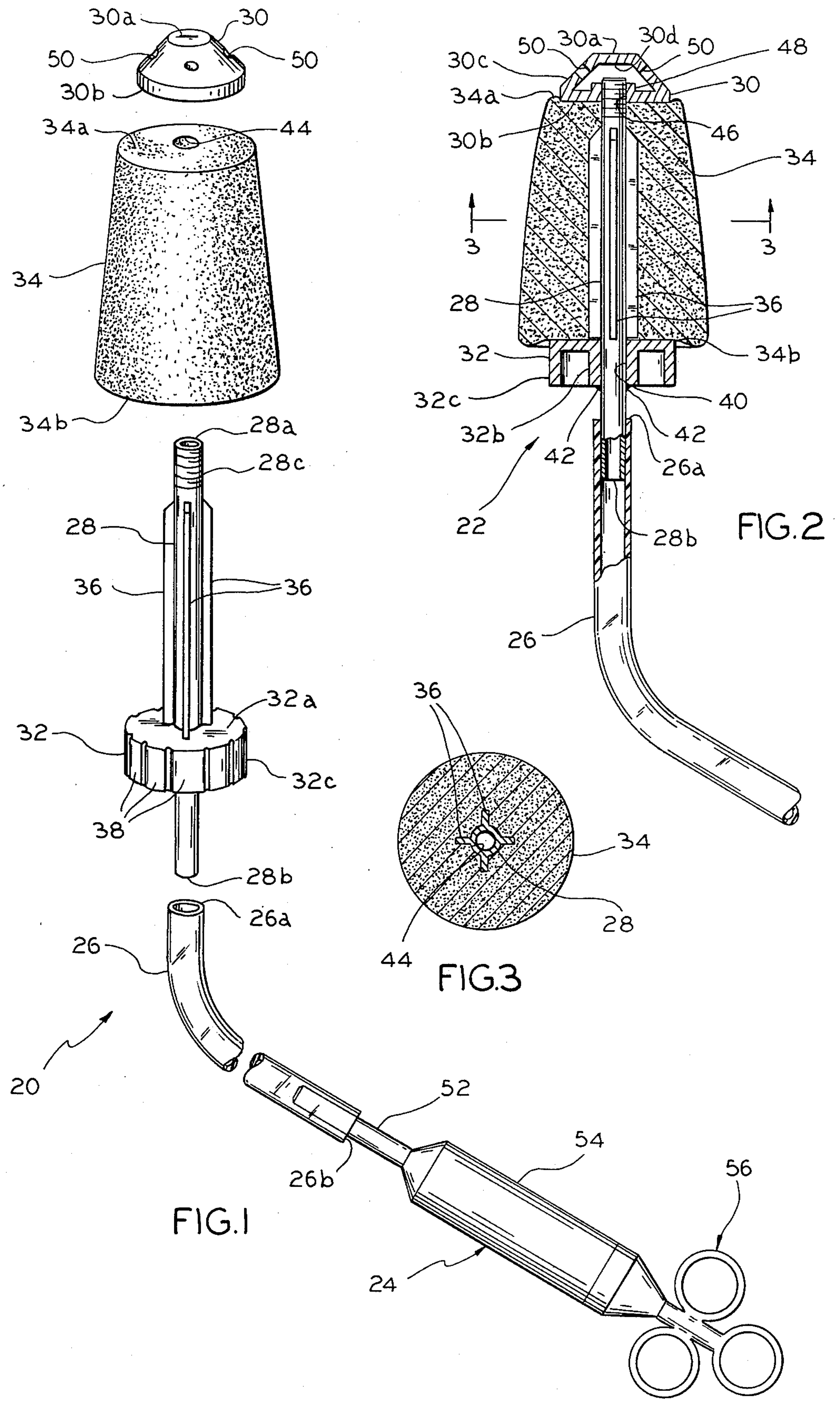
FIG. 1 is an exploded perspective view, with a part broken, of a preferred embodiment of the sanitation apparatus, which is designed for professional use.
FIG. 2 is a longitudinal sectional and partly elevational view of a cleaning instrument thereof.
FIG. 3 is a cross-sectional view of the cleaning instrument, taken substantially on line 3—3 of FIG. 2.

Referring to FIGS. 1–3 of the drawings, a preferred equine sanitation apparatus 20 designed especially for professional use includes a cleaning instrument 22, a liquid supply instrument 24, and a flexible tube or conduit 26 connecting the two instruments. The cleaning instrument 22 includes a first liquid supply tube 28 having distal and proximal ends **28*a* and 28*b*, respectively, a nozzle 30 fixed on the distal end 28*a* of the first supply tube, manipulating or handle means in the form of a knob 32 fixed on the first supply tube 28 in spaced relation to the proximal end 28*b* thereof, and a sponge 34 fixed on the first supply tube 28 between the nozzle 30 and the knob 32. The liquid supply instrument 24** is supplied in the form of a conventional dose syringe or the like.

In the embodiment of FIGS. 1–3, the first supply tube 28 has a threaded section **28*c* at its distal end 28*a*. Four elongated vanes 36 are integral with the tube 28 and extend radially outwardly therefrom at equal angles of 90° therearound. The vanes 36 extend longitudinally of the tube 28 from the threaded section 28*c* towards the proximal end 28*b* and spaced inwardly therefrom. In this embodiment, the tube section between the proximal end 28*b* and the vanes 36** is smooth and cylindrical.

The knob 32 is generally cylindrical, and it includes a substantially flat clamping base or wall portion **32*a* at its distal end, and inner and outer annular mounting and skirt portions 32*b* and 32*c*, respectively, which are integral with the base portion 32*a* and extend perpendicularly therefrom. The skirt portion 32*c* is provided with a succession of undulations 38 forming the outer surface thereof, for manual gripping purposes. The mounting portion 32*b* defines a cylindrical opening 40 through the knob 32, as seen in FIG. 2**.

The smooth portion of the first supply tube 28, adjacent to the proximal end **28*b*, is received in the knob opening 40, with the knob 32 disposed adjacent to the vanes 36 and its base portion 32*a* facing towards the distal end 28*a* of the supply tube. The knob 32 is fixed to the tube 28 by any suitable means, such as welding, shrinking, pinning, or other fastening means. The illustrative fastening means are welds 42, which bond the mounting portion 32*b* to the supply tube 28**.

The sponge 34 is an elongated, slightly tapered substantially frusto-conical body having an axial internal longitudinal bore 44 therein. The bore 44 extends between substantially flat and parallel circular distal and proximal end surfaces **34*a* and 34*b***, respectively, which are substantially perpendicular to the longitudinal axis of the sponge. The sponge may be a natural sponge or an artificial sponge, such as a cellulosic sponge.

The sponge 34 is mounted on the first supply tube 28 by inserting the distal end **28*a* of the tube into the bore 44 of the sponge at the proximal end surface 34*b*, until that end surface is seated on the base portion 32*a* of the knob 32. The vanes 36 forcibly penetrate the side wall of the bore 44 so as to extend into the body of the sponge, as illustrated in FIG. 3, thereby fixing the sponge to the supply tube so as to prevent relative rotation therebetween. Alternatively, a bore may be provided in the sponge, in a cross-sectional configuration like that of the outer periphery of the supply tube 28 and the vanes 36** thereon, for reception of the tube and vanes therein.

The nozzle 30 is a generally frusto-conical member, which has flat circular parallel distal and proximal end walls **30*a* and 30*b*, respectively, and an outwardly converging frusto-conical side wall 30*c* extending therebetween, to define therewith a hollow chamber 30*d* in the nozzle. An internally-threaded sleeve portion 48 is integral with the proximal end wall 30*b*, and it defines an axial opening 46 extending through the wall. A series of jet discharge openings 50 is provided in the side wall 30*c*, the openings extending through the wall in open communication with the chamber 30*d*. In the illustrative embodiment, there are four such openings 50, which extend angularly outwardly with respect to the longitudinal axis of the nozzle 30, and in the direction of the distal end wall 30*a*. The openings 50 are disposed equiangularly about the longitudinal axis of the nozzle 30**.

The nozzle 30 is engaged with the first supply tube 28 after the sponge 34 is mounted on the tube, by threading the sleeve portion 48 of the nozzle onto the threaded section **28*c* of the tube. The nozzle chamber 30*d* then is in open communication with the supply tube 28. The proximal end wall 30*b* of the nozzle provides a clamping surface which parallels the base portion 32*a* of the knob 32, and the nozzle 30 is threaded on the tube so as to clamp the sponge 34 between it and the knob. The nozzle 30 and the knob 32 thus serve to prevent longitudinal movement of the sponge 34 on the first supply tube 28, while the vanes 36** prevent rotational movement of the sponge on the tube, whereby the sponge is fixed on the tube.

The first supply tube 28 preferably is a relatively rigid or stiff tube, to provide support for the other elements of the cleaning instrument 22 and means for attaching the relatively flexible tube 26, hereinafter also referred to as the second supply tube, to the cleaning instrument 22. In the preferred illustrative structure, the first supply tube 28 with integral vanes 36, the nozzle 30, and the knob 32 are constructed of stainless steel. The sponge 34 is replaceable after each use, and the remainder of the instrument 22 may be used as permanent equipment, having sturdy construction and being nonporous and readily maintained in clean and sterile condition.

The flexible second supply tube 26 preferably is made of light-transmitting plastic, especially clear plastic, and it has an internal diameter approximately the same as or slightly smaller than the external diameter of the first supply tube 28 at its proximal end **28*b*. The distal end 26*a* of the second supply tube is pushed over the proximal end 28*b* of the first supply tube, so that the distal end of the second supply tube is mounted on the first supply tube in telescoping relation thereto and in susbstantially liquid-tight fit. The second supply tube 26 is provided in a length suitable for reaching from the sheath of an animal to a convenient location for holding the syringe 24, and it is flexible enough to provide mobility and maneuverability, as conditions necessitate. The light-transmitting characteristic of the second supply tube 26** is provided in the preferred embodiments, to enable the user to determine whether or not any solids are present in flushing liquid flowing therethrough, as described hereinafter.

Figure 10:
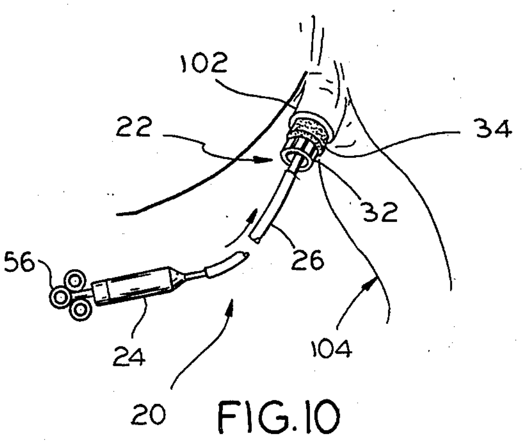
Figure 12:
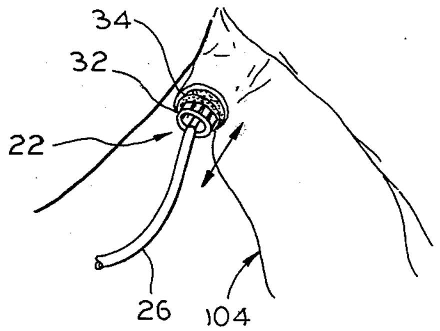

The syringe 24 preferably is a dose syringe of about 16-ounce capacity, and it includes a spout 52. The proximal end **26*b* of the second supply tube telescopically receives a portion of the spout 52 therein, in a substantially liquid-tight fit. The syringe 24** includes a reservoir 54 and a finger grip 56, the latter accommodating the thumb and two fingers of the hand. The finger grip 56 is connected to a suitable internal plunger, not visible, for both expelling liquid in the reservoir 54 and drawing liquid into the reservoir. Thus, by moving the finger grip 56 outwardly, with the spout 52 in communication with a liquid source, the liquid will be drawn into the reservoir 54. When the grip 56 is moved inwardly, the liquid in the reservoir 54 will be expelled in a stream issuing from the spout 52. When the apparatus 20 is assembled, as illustrated in FIG. 10, liquid may be pumped back and forth therethrough, from the reservoir 54 to the nozzle 30.

Figure 4:
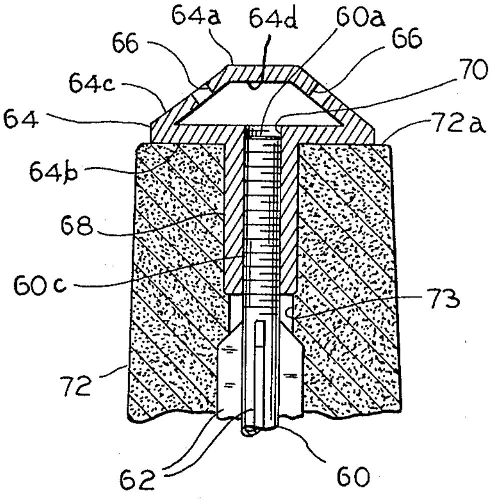
FIG. 4 is a fragmentary longitudinal sectional and partly elevational view of a modification of the cleaning instrument.
Figure 5:
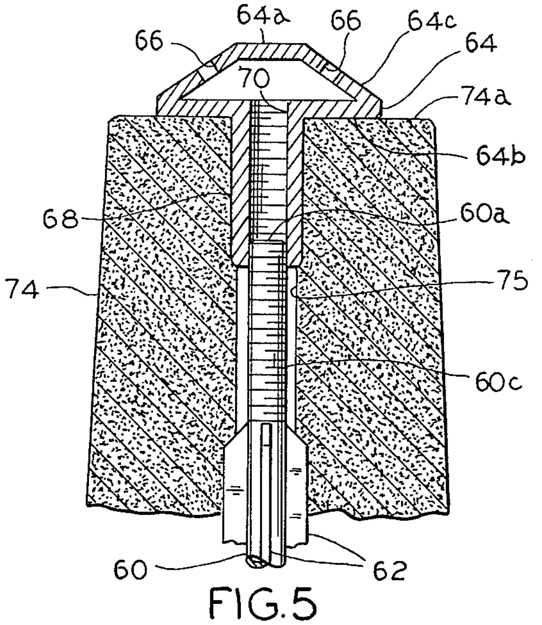
FIG. 5 is a view similar to FIG. 4, but illustrating the cleaning instrument as employed with an older animal.
Figure 6:
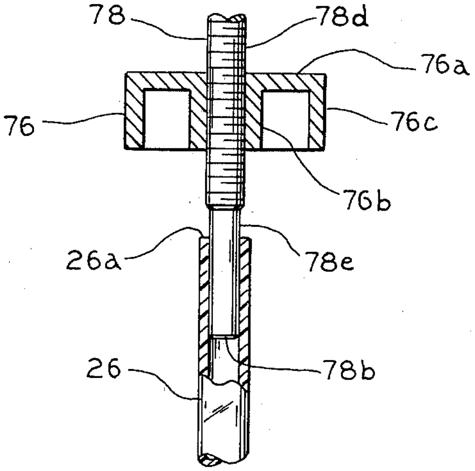
FIG. 6 is a fragmentary view of another modification of the cleaning instrument.

It is preferable to employ the new sanitation apparatus in three sizes, namely, a small size for colts, an intermediate size for two to three year old horses, and a large size for mature horses. The several sizes may be provided by one apparatus, which is constructed for accommodating three sponge sizes, having progressively greater length and width dimensions. FIGS. 4–6 illustrate modifications which have adjustment means to accommodate the three sponge sizes.

Referring to FIGS. 4 and 5, a first supply tube 60 having vanes 62 is constructed like the first supply tube 28 and vanes 36 of FIGS. 1–3, but with a greater number of threads in the threaded section 60*c* at the distal end 60*a* of the supply tube. A nozzle 64 having jet openings 66 in a frusto-conical side wall 64*c* thereof is constructed like the nozzle 30 of FIGS. 1–3, but is provided with an elongated axially outwardly extending internally-threaded sleeve 68, which extends inwardly in the apparatus. The sleeve 68 is integral with a proximal end wall 64*b* of the nozzle 64, and defines an axial circular opening 70 therethrough. The nozzle 64 is completed by a distal end wall 64*a*, parallel to the proximal end wall 64*b* and perpendicular to the longitudinal axis of the nozzle, which is coincident with the longitudinal axis of the sleeve 68. The walls 64*a*, 64*b* and 64*c* define a hollow chamber 64*d*.

FIG. 4 illustrates the apparatus as it appears when a small size sponge 72, having a longitudinal axial bore 73, is employed therein, for use with colts. The threaded tube section 60*c* then is threaded nearly completely into the nozzle sleeve 68, in the illustration, so as to clamp the relatively short sponge 72 between the nozzle 64 and a knob like the knob 32 in FIGS. 1 and 2. FIG. 5, on the other hand, illustrates the apparatus at it appears when a large size sponge 74, having a longitudinal axial bore 75, is employed therein, for using the apparatus on a mature horse. In this case, only a minor portion of the threaded tube section 60*c* extends into the sleeve 68 of the nozzle 64, to accommodate the relatively long sponge 74. Again, the sponge is clamped between the nozzle 64 and a knob, such as the knob 32 in FIGS. 1 and 2. It will be apparent that a sponge intermediate in size between the sponges 72 and 74 of FIGS. 4 and 5 may be provided in the apparatus, in like manner, for use in young horses. In such case, the sleeve 68 and the threaded tube section 60*c* received therein will telescope for a distance intermediate the distances which the parts telescope in the respective assemblies of FIGS. 4 and 5.

As an example of preferred dimensions for use with a mature horse, and referring to FIGS. 1 and 2, the length dimension measured from the distal end wall 30*a* of the nozzle 30 to the proximal end surface 34*b* of the sponge 34 is about 5 inches, and the diameter of the proximal end surface 34*b* of the sponge is about 3 inches. The dimensions decrease for younger horses and colts.

FIG. 6 illustrates structure for adjustably mounting a knob 76 on a first supply tube 78, which may be provided together with the remaining structure of FIGS. 1–3 and/or FIGS. 4 and 5. This structure includes a threaded section 78*d* on the supply tube 78, in adjacent spaced relation to the proximal end 78*b* of the tube. The knob 76, similarly to the knob 32 of FIGS. 1–3, includes a clamping base or wall portion 76*a*, and inner and outer annular mounting and skirt portions 76*b* and 76*c*, respectively. The knob 76 differs from the knob 32 of the first embodiment in having its mounting portion 76*b* internally threaded for engagement with the threaded section 78*d* of the first supply tube 78. The first supply tube 78 is provided with a smooth cylindrical section 78*c* at its proximal end 78*b*, for telescopic reception of the flexible second supply tube 26 thereon, in the same manner as in the embodiment of FIGS. 1–3.

With the provision of the structure of FIG. 6, any of the sponges 34, 72, and 74 may be mounted on the first supply tube 78 by inserting the proximal end 78*b* of the tube into the corresponding bore 44, 73, or 75 of the sponge at its distal end surface 34*a*, 72*a*, or 74*a*. If desired, a nozzle such as the nozzle 30 may be fixed to the distal end of the first supply tube 78 by any suitable fastening means, without need for a threaded connection, inasmuch as the threaded connection between the knob 76 and the threaded section 78*d* provides both for mounting the sponge and for adjustment of the distance between the knob and the nozzle to accommodate the length of the sponge being used.

Figure 7:
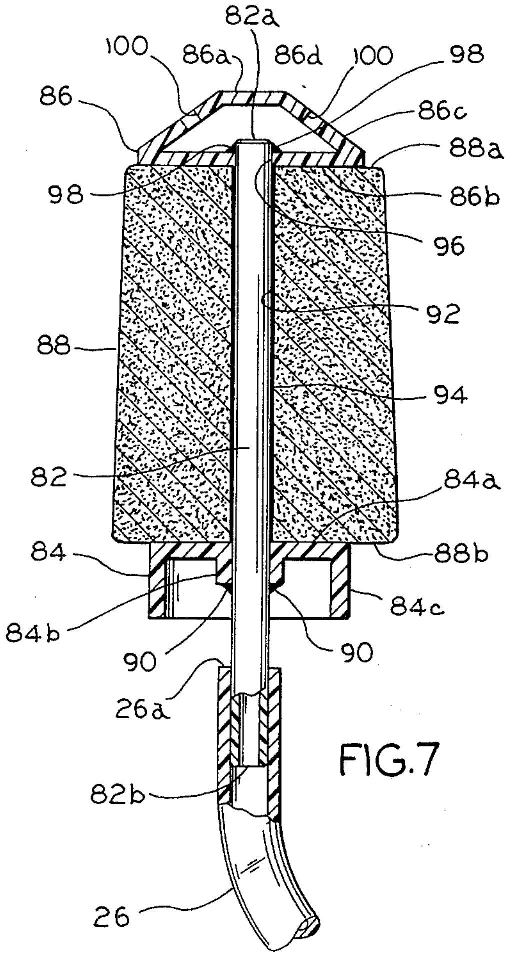
FIG. 7 is a longitudinal sectional and partly elevational view of another embodiment of the cleaning instrument, which is disposable in nature.

FIG. 7 illustrates a cleaning instrument 80 which is constructed of plastic parts, to render it economical and disposable in nature. This embodiment of the cleaning instrument includes a relatively rigid or stiff plastic first supply tube 82, a plastic knob 84 affixed to the supply tube adjacent to and spaced from its proximal end 82*b*, a plastic nozzle 86 affixed to the supply tube at its distal end 82*a*, and a sponge 88 affixed to the supply tube between the knob and the nozzle. The proximal end 82*b* of the supply tube 82 is inserted into the flexible second supply tube 26 in the same manner as in the embodiment of FIGS. 1–3, and the second supply tube 26 in turn may be connected to a dose syringe 24 or the like, as illustrated in FIG. 1.

The knob 84 essentially is the same as the knob 32 of the first embodiment, except for the difference in materials, and it includes a base portion 84*a*, and inner and outer annular mounting and skirt portions 84*b* and 84*c*, respectively. It and the remaining plastic parts may be affixed together in any of the known ways suitable for the purpose, and in the illustrative embodiment, the mounting portion 84*b* of the knob is cemented to the first supply tube 82, as represented at 90. The sponge 88 is cemented to the first supply tube 82 along the length of a longitudinal cylindrical bore 92 in the sponge, as represented at 94.

The nozzle 86 essentially is like the nozzle 30 of the first embodiment, being of frusto-conical shape, and including jet discharge openings 100 arranged in a frusto-conical side wall 86*c* in the same manner as the openings 50 in the first embodiment. The nozzle 86 is provided with a central circular opening 96 in its proximal end wall 86*b*, which receives the distal end 82*a* of the first supply tube 82. The proximal end wall 86*b* is cemented to the distal end 82*a*, as represented at 98. The nozzle 86 is completed with a distal end wall 86*a*, which defines a hollow chamber **86*d* together with the remaining walls 86*b* and 86*c*. The chamber 86*d* is in open communication with the supply tube 82 and the openings 100**.

Figure 8:
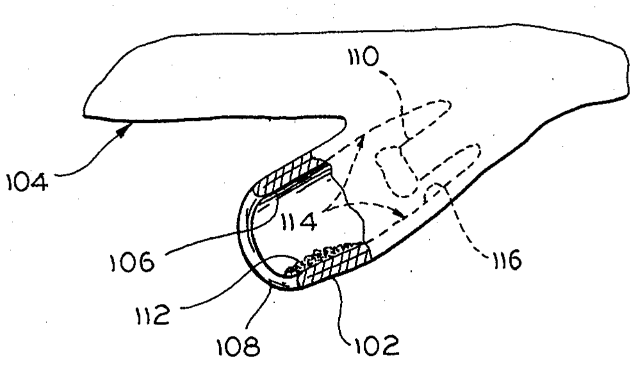
FIG. 8 is a fragmentary elevational and partly sectional view, showing the sheath of a horse, with a portion broken away to reveal the sheath cavity.

Referring to FIG. 8, the sheath 102 of a horse 104 is illustrated. The prepuce or foreskin 106 extends inwardly from the mouth 108 or opening in the sheath, to the penis 110, which in a mature horse may be 6–8 inches inwardly from the mouth 108. Smegma may be found to cover the prepuce, with relatively hard crustaceous deposits 112 at the mouth.

Figure 9:
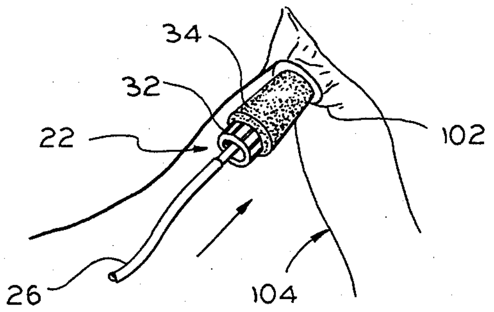
FIGS. 9–12 are fragmentary views illustrating parts of the animal including the sheath, and the manner in which the sanitation apparatus is employed to cleanse the sheath, the views also illustrating a preferred sequence of steps in the new method.

The cleaning instrument 22, representative of the several embodiments, is prepared for use in cleaning the sheath 102 by immersing it in a container of soapy water, the soap or shampoo of which cuts body oil. The sponge 34 is impregnated with the solution, so that it is ready for insertion in the sheath 102. The cleaning instrument 22 is grasped by the knob 32, and manipulated so as to insert its distal end through the mouth 108 of the sheath and into the cavity 116 therein. The instrument 22 is inserted up to about one inch short of the penis 110, generally in the manner illustrated in FIGS. 9 and 10. The sponge 34 brushes the wall of the cavity as it is being inserted, and it substantially closes the opening through the mouth 108. The knob 32 remains outside of the sheath.

Conveniently, the spout 52 of the syringe 24 next is immersed in the soapy solution, and the finger grip 56 is moved outwardly to fill the reservoir 54 with the solution. The spout 52 then is inserted in the proximal end **26*b* of the second supply tube 26, to complete the assembly of the apparatus 20, as illustrated in FIG. 10. Pressure on the finger grip 56 causes liquid in the reservoir 54 to be discharged from the spout 52, from whence the liquid is conducted through the second supply tube 26 and the first supply tube 28, to the hollow chamber 30*d* in the nozzle 30. Under the pressure exerted at the finger grip 56, the liquid is discharged through the openings 50 in jet streams, which impinge on the prepuce 106 at locations disposed laterally of the nozzle 30, such as the locations indicated by the number 114 in FIG. 8. The flow of liquid from the first supply tube 28 thus is directed angularly outwardly from the longitudinal axes of the nozzle 30 and the tube 28, so as to avoid impingement of a liquid stream therefrom directly on the organ 110** in the sheath, thereby avoiding irritation of the organ.

Sufficient solution is pumped in from the syringe 24 to fill the sheath cavity 116 and soak the sponge 34, this condition being indicated when solution comes out of the cavity around the sponge. The soapy solution then is pumped in and out of the cavity 116, through the nozzle openings 50, to flush the cavity. Flushing is effected by reciprocating the finger grip 56 on the syringe 24, until the solution comes dirty, as indicated by the presence of sediment in viewing the solution through the light-transmitting wall of the second supply tube 26. This usually occurs with about three to four pumpings.

Figure 11:
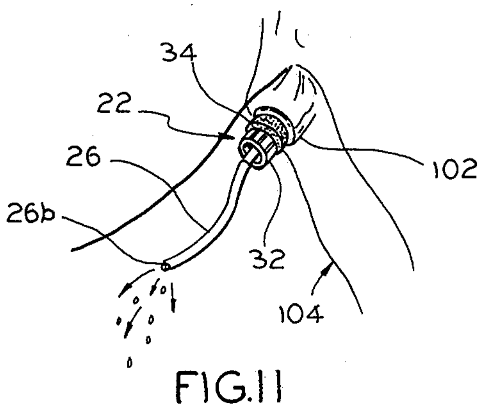

When the solution becomes dirty, the syringe 24 is removed, and the remainder of the apparatus is allowed to drain from the proximal end **26*b* of the second supply tube 26, as illustrated in FIG. 11. The syringe 24 is filled with fresh solution, reattached, and the foregoing process is repeated, until no more sediment appears. Flushing once more usually suffices, inasmuch as the second flushing usually shows clean or contains only a small amount of sediment. After draining once more, as illustrated in FIG. 11, it is preferred to allow the cleaning instrument 22 to remain in the same position in the sheath 102 for about 5–10 minutes, so as to soak the hard crusts of smegma 112, near the mouth 108** of the sheath, for the purpose of softening the crusts and breaking them down.

Following the soaking period, the user grasps the knob 32 in one hand, and preferably moves the cleaning instrument 22 vigorously in and out of the sheath 102, to dislodge and remove the smegma. Removal of the smegma is ascertained by pulling the instrument 22 out of the sheath and checking inside of the sheath with the hand. It may be necessary to reciprocate the instrument 22 and the sheath about 10 to 20 times to remove the smegma. Alternatively, or in conjunction with the reciprocation of the cleaning instrument 22, the instrument may be rotated to loosen and remove the smegma, by turning the knob 32 with the hand.

When the sheath shows clean after undergoing the foregoing steps, the flushing process is repeated, using fresh water. The water may contain an antiseptic, especially when cleaning a stallion. The flushing liquid is checked for sediment, and flushing is continued until the liquid is clean.

When cleaning a stallion, part of the foregoing procedure may be dispensed with where the stallion is active, inasmuch as no hard smegma forms. Stallions preferably are cleaned before and after breeding.

The new sanitation apparatus also serves advantageously for douching mares. It minimizes irritation of the mucous membranes and provides a more efficient instrument. For this use, the cleaning instrument 22, or other cleaning instrument, such as illustrated in FIG. 7, is soaked in antiseptic solution and then inserted into the vagina through the vulva. The syringe 24 is filled with the antiseptic solution and attached to the second supply tube 26, in turn attached to the first supply tube 28. The vaginal cavity or vault is flushed by reciprocating the finger grip 56, and the apparatus is removed. The sponge next is squeezed to remove the liquid therefrom, and then reinserted into the vagina for absorbing the remaining solution therein.

The sponge 34 fits easily into the vagina, and avoids the prior contact of a tube with the mucous membranes, which may irritate them. The sponge also furnishes a convenient instrumentality for removing the antiseptic solution after the treatment.

While preferred embodiments of the apparatus and method of the invention have been illustrated and described, it will be apparent to those skilled in the art that various changes and modifications may be made therein within the spirit and scope of the invention. It is intended that all such changes and modifications be included within the scope of the appended claims.

I claim:

1. Equine sanitation apparatus which comprises, in combination, a supply tube having distal and proximal ends, nozzle means on the distal end of said tube and defining discharge openings therein, manipulating means on said tube and spaced apart longitudinally from said nozzle means in the direction of the proximal end of the tube, and a sponge on said tube between said nozzle means and said manipulating means, whereby said manipulating means may be manually operated to insert said nozzle means and said sponge into an equine sheath cavity and manipulate the sponge therein, and a liquid may be supplied to and exhausted from the cavity via said tube and said nozzle means so as to flush the cavity through said discharge openings and thereby loosen smegma in the cavity and remove the smegma therefrom through the discharge openings.

2. Apparatus as defined in claim 1 and wherein said nozzle means delivers liquid through said discharge openings only in directions away from the longitudinal axis of said tube.

3. Apparatus as defined in claim 1 or 2 and including a liquid supply instrument for supplying a liquid to said tube and exhausting the liquid therefrom.

4. Apparatus as defined in claim 1 or 2 and including thread means interengaging said tube and at least one of said nozzle means and said manipulating means, and means defining an internal longitudinal bore in said sponge, whereby said sponge is mounted on said tube by inserting the tube through said bore from a tube end adjacent to said threaded means.

5. Apparatus as defined in claim 4 and wherein said nozzle means and said manipulating means are adapted for clamping said sponge between them.

6. Apparatus as defined in claim 5 and wherein said thread means provides means for adjustment of the distance between said nozzle means and said manipulating means, whereby sponges having a plurality of lengths may be mounted alternatively on said tube.

7. Apparatus as defined in claim 4 and including longitudinal blade means on said tube and interengaging the tube and said sponge for conjoint rotation.

8. Equine sanitation apparatus which comprises, in combination, a relatively rigid first supply tube having distal and proximal ends, nozzle means on the distal end of said first supply tube and defining discharge openings therein, knob means on said first supply tube and spaced apart longitudinally from said nozzle means in the direction of the proximal end of the tube, a sponge on said first supply tube between said nozzle means and said knob means, a relatively flexible second supply tube having distal and proximal ends, the distal end of said second supply tube being adapted for telescopic connection to the proximal end of said first supply tube, and syringe means for supplying a liquid to the proximal end of said second supply tube and exhausting the liquid therefrom, whereby said knob means may be manually operated to insert said nozzle means and said sponge into an equine sheath cavity and manipulate the sponge therein, and a liquid may be supplied to and exhausted from the cavity via said first and second supply tubes and said nozzle means so as to flush the cavity through said discharge openings and thereby loosen smegma in the cavity and remove the smegma therefrom through the discharge openings.

9. Apparatus as defined in claim 8 and wherein said nozzle means delivers liquid through said discharge openings only in directions away from the longitudinal axis of said first supply tube.

10. Apparatus as defined in claim 8 or 9 and including thread means interengaging said first supply tube and at least one of said nozzle means and said knob means, and means defining an internal longitudinal bore in said sponge, whereby said sponge is mounted on said first supply tube by inserting the tube through said bore from a tube end adjacent to said thread means.

11. Apparatus as defined in claim 10 and wherein said nozzle means and said knob means are adapted for clamping said sponge between them.

12. A method for cleaning internally an equine sheath which comprises the steps of:

inserting in the sheath cavity a sponge having a liquid supply tube extending therethrough for discharge into the sheath cavity from a distal end of the tube, flushing the sheath cavity with liquid delivered and exhausted through the tube to loosen smegma in the cavity and remove the smegma therefrom in the exhaust liquid, and scrubbing the surface of the sheath cavity with the sponge to break up crustaceous smegma for removal thereof.

13. A method as defined in claim 12 and wherein said sheath cavity flushing is effected by delivering liquid into said sheath cavity from nozzle means on the distal end of the tube, which nozzle means defines discharge openings therein through which the flow of liquid from the tube is directed so as to avoid impingement of a liquid stream therefrom directly upon the organ in the sheath.

14. A method as defined in claim 12 or 13 and wherein said insertion and said scrubbing are effected by manually operating manipulating means which are provided for that purpose on said tube between said sponge and a proximal end of the tube.

15. A method as defined in claim 12 or 13 and wherein said sheath cavity flushing is effected by supplying liquid to said tube from a liquid supply instrument.

16. A method as defined in claim 12 or 13 and wherein said sheath cavity flushing is effected by supplying liquid to said tube and exhausting the liquid therefrom by manual operation of syringe means in communication with the tube.

17. A method for cleaning internally an equine sheath which comprises the steps of:

providing a sponge having a liquid supply tube extending therethrough and nozzle means on a distal end of the tube, said nozzle means defining discharge openings therein, said tube having manipulating means thereon between said sponge and a proximal end of the tube, manually operating said manipulating means to insert said sponge in the sheath cavity for discharging liquid through said discharge openings directly into the cavity, providing a liquid supply instrument in communication with said tube at its proximal end, manually operating said liquid supply instrument to supply liquid to said tube and exhaust the liquid therefrom, so as to flush the sheath cavity through said discharge openings and thereby loosen smegma in the cavity and remove the smegma therefrom through the discharge openings, and manually operating said manipulating means to scrub the surface of the sheath cavity with the sponge to break up crustaceous smegma for removal thereof.

18. A method as defined in claim 17 and wherein said liquid supply instrument comprises syringe means.

19. A method as defined in claim 17 or 18 and wherein the liquid delivered into the sheath cavity is directed through said discharge openings so as to avoid impingement of a liquid stream directly upon the organ in the sheath.

* * * * *